United States Patent [19]

Kikuchi et al.

[11] Patent Number: 4,943,416
[45] Date of Patent: Jul. 24, 1990

[54] AUTOMATIC URINALYSIS SYSTEM

[75] Inventors: Makoto Kikuchi, Mitaka; Manabu Harada, Tokyo, both of Japan

[73] Assignee: Kabushiki Kaisha Marukomu, Tokyo, Japan

[21] Appl. No.: 100,224

[22] Filed: Sep. 23, 1987

[51] Int. Cl.$^5$ ............................................. G01N 35/00
[52] U.S. Cl. ....................................... 422/63; 422/64; 422/65; 422/66; 422/67; 422/68.1
[58] Field of Search ...................... 4/144.1, 144.2, 365, 4/DIG. 5; 128/760–763; 422/63–68; 436/43, 44, 46, 48

[56] References Cited

U.S. PATENT DOCUMENTS

| | | | |
|---|---|---|---|
| 2,035,567 | 3/1936 | Piper | 4/DIG. 5 |
| 3,620,678 | 11/1971 | Guigan et al. | 422/66 |
| 3,684,452 | 8/1972 | Bessman | 422/64 |
| 3,918,910 | 11/1975 | Soya et al. | 422/66 X |
| 4,224,032 | 9/1980 | Glover | 436/46 |
| 4,336,438 | 6/1982 | Uehara et al. | 250/492.2 X |
| 4,420,566 | 12/1983 | Jessop | 436/46 |

OTHER PUBLICATIONS

Huttunen et al.; Simple Method for Increasing Reliability in Diagnosis of Urinary Infection; The Lancet 1–3–70, p. 22.
Ames, Clinitek 10 System, 1984, 6 pages.
DIC, Mini Aution Analyzer, 4 pages, (no translation).

Primary Examiner—Michael S. Marcus
Attorney, Agent, or Firm—Robert F. Ziems

[57] ABSTRACT

An automatic urinalysis system which can be readily installed at an excretion site such as a toilet and by which means a subject itself can test its urine easily at any time and can obtain results of such test. The system comprises a sample collecting means for collecting a sample of urine within a stool or the like at an excretion site, a guiding means for introducing the collected urine sample into a testing area within a body of the system, a urine testing element located within the system body, a contacting means for automatically contacting the urine testing element with the urine sample in the testing area, a urine testing means for automatically testing the urine testing element contacted with the urine sample by the contacting means, a display means for displaying test data from the urine testing means, and a discharging means for discharging the urine sample into the stool after the urine sample has been contacted by the urine testing element.

21 Claims, 6 Drawing Sheets

AUTOMATIC URINALYSIS SYSTEM

BACKGROUND OF THE INVENTION

1. Field of the Invention

This invention relates to a system for automatically testing urine excreted from a human body, and more particularly to a system for use in a toilet for automatically analyzing and measuring urine in response to a coin thrown into the system or in response to depression of a start switch when the toilet is used.

2. Description of the Prior Art

The society in which we live is called information society, and in such society, information also regarding health is abundant so that there are many people who know analysis values of their own urine or the necessity of such analysis even though they are healthy. Much more, people who have some disease are very sensitive to such kind of information, and according to a disease, their conditions of bodies need be tested of urine day by day in order to recognize the same with numerical values.

Urine can be tested individually by each person using paper for testing of urine which can be purchased, for example, at a drugstore. Testing using a urine testing element such as testing paper or a reagent is generally performed for several items including (1) PH, (2) glucose, (3) protein, (4) occult blood, (5) urobilinogen, (6) ketone, (7) bilirubin, (8) nitrite, and (9) chlorine.

Anyway, since the color of testing paper or a reagent changes as it contacts with urine to be tested, the urine can be tested by comparing the color of the testing paper or reagent with predetermined reference color tones.

While each individual can test its urine using a urine testing element such as testing paper or a reagent in this manner, actually such a urine testing element is not frequently used from several reasons: for example, because they are not known to people; because they are inconvenient and troublesome to use; or because they feel unsanitary.

Accordingly, each individual must take the trouble to go to a hospital or a medical testing center in order to undergo a test of its urine.

Further, although several automatic urine analyzers have already been made public and are practically used in hospitals and medical testing centers, they cannot be installed at a urine excretion site, and accordingly analytical testing of urine cannot be done without delay at such a urine excretion site.

Meanwhile, automatic determination of a developed color of a reagent body for testing of urine such as, for example, urine testing paper is enabled by a well known absorption photometry which is a method of measuring a ratio wherein light of a peculiar wavelength zone corresponding to a developed color is absorbed. In order to effect such an absorption photometry, an integrating sphere system is conventionally employed. In the integrating sphere system, when reflected light from a reagent body for testing of urine is to be measured, light is scattered and multiple reflected by a layer of powder of MgO (magnesium oxide) or a like substance applied to an inner wall of a spherical body in order that the measurement may not be influenced by a bias or some other factor of such reflected light.

SUMMARY OF THE INVENTION

It is an object of the present invention to provide an automatic urinalysis system which can easily and frequently test and analyze urine and can provide information of results of such analysis to a subject at an excretion site such as a toilet of a hotel, a department store, a firm or a house of the subject itself at which the automatic urinalysis system is installed without the necessity for the subject to take the trouble to go to a hospital or a medical testing center in order to undergo a medical testing of urine performed thereat by a doctor and/or a nurse.

It is another object of the present invention to provide an inexpensive, useful automatic urinalysis system which has a long life, eliminates maintenance, and is high in accuracy.

In order to attain the objects, according to the present invention, there is provided an automatic urinalysis system for use at an excretion site such as a toilet, comprising a sample collecting means for collecting a sample of urine consisting of pure urine or a mixture containing urine within a stool or a like member at an excretion site at which the automatic urinalysis system is installed and for taking the collected urine sample into the automatic urinalysis system, a guiding means for introducing the urine sample collected by the sample collecting means into a testing area within a body of the automatic urinalysis system, a urine testing element located within the body, a contacting means for automatically contacting the urine testing element with the urine sample in the testing area, a urine testing means for automatically testing the urine testing element contacted with the urine sample by the contacting means, a display means for displaying test data from the urine testing means, and a discharging means for discharging the urine sample to a discharge location such as the stool after the urine sample has been contacted by the urine testing element.

As described above, while several automatic urine analyzers have already been made public and are practically used in hospitals and medical testing centers, none of them can test urine without delay at a urine excretion site nor can inform of results of the test. To the contrary, with the automatic urinalysis system of the present invention, it can be installed at any urine excreting side, and where it is installed at such a site, it can be used easily by any individual. Thus, it can test urine readily and inform of results of the test without delay.

In the automatic urinalysis system of the present invention, the integrating sphere method described above can be employed as a method of measuring a changed color tone density of a urine testing element where the urine testing element is of the type which is changed in color by a component of urine.

The above and other objects, features and advantages of the present invention will become apparent from the following description and the appended claims, taken in conjunction with the accompanying drawings.

DESCRIPTION OF THE PREFERRED EMBODIMENTS

Figure 1:
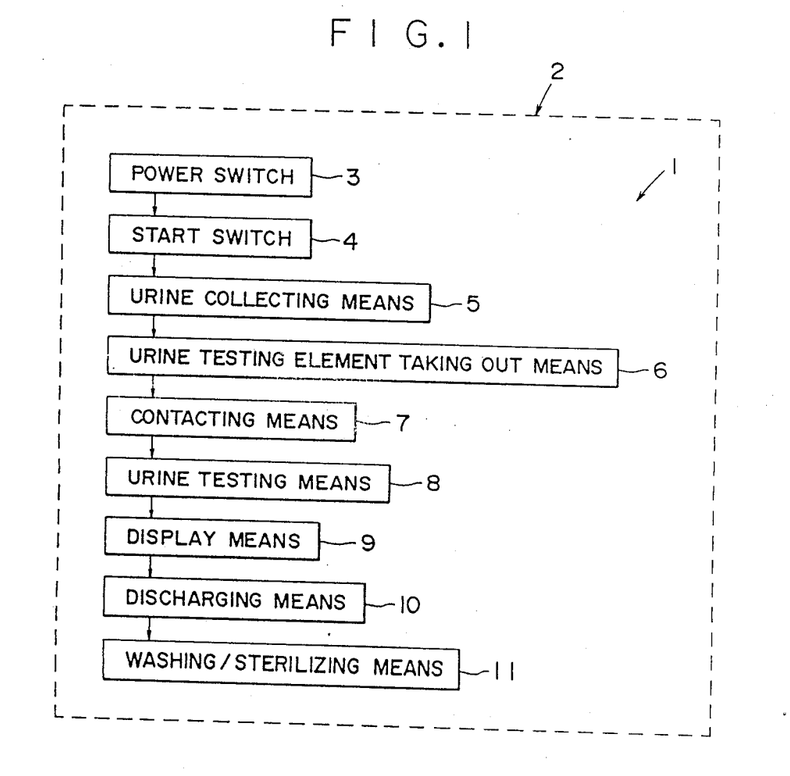
FIG. 1 is a block diagram schematically showing general construction of an automatic urinalysis system according to the present invention.

Referring first to FIG. 1, there is shown general construction of an automatic urinalysis system according to the present invention. The automatic urinalysis system generally denoted at 1 is installed at a urine excretion site 2 such as a toilet room. The automatic urinalysis system 1 starts its operation when a start switch 4 is closed after a power switch 3 has been closed. Upon closing of the start switch 4, a sample of urine or a mixture containing urine is collected from within a stool of the excretion site 2 and stored into a storage chamber by a urine collecting means 5 of the automatic urinalysis system 1. After then, a urine testing element taking out means 6 takes out a urine testing element from within a urine testing element storage box of the automatic urinalysis system 1. The urine testing element thus taken out is fed into the storage chamber and immersed into the urine sample within the storage chamber by a contacting means 7. The urine testing element then undergoes an analytical test by a urine testing means 8, and analyzed test data of the urine thus obtained is then indicated on a display means 9 while the urine sample after such analytical testing is then discharged into the stool by a discharging means 10. After then, the storage chamber and some other components of the automatic urinalysis system 1 which have contacted with the urine are washed and/or sterilized by a washing and/or sterilizing means 11.

Figure 2:
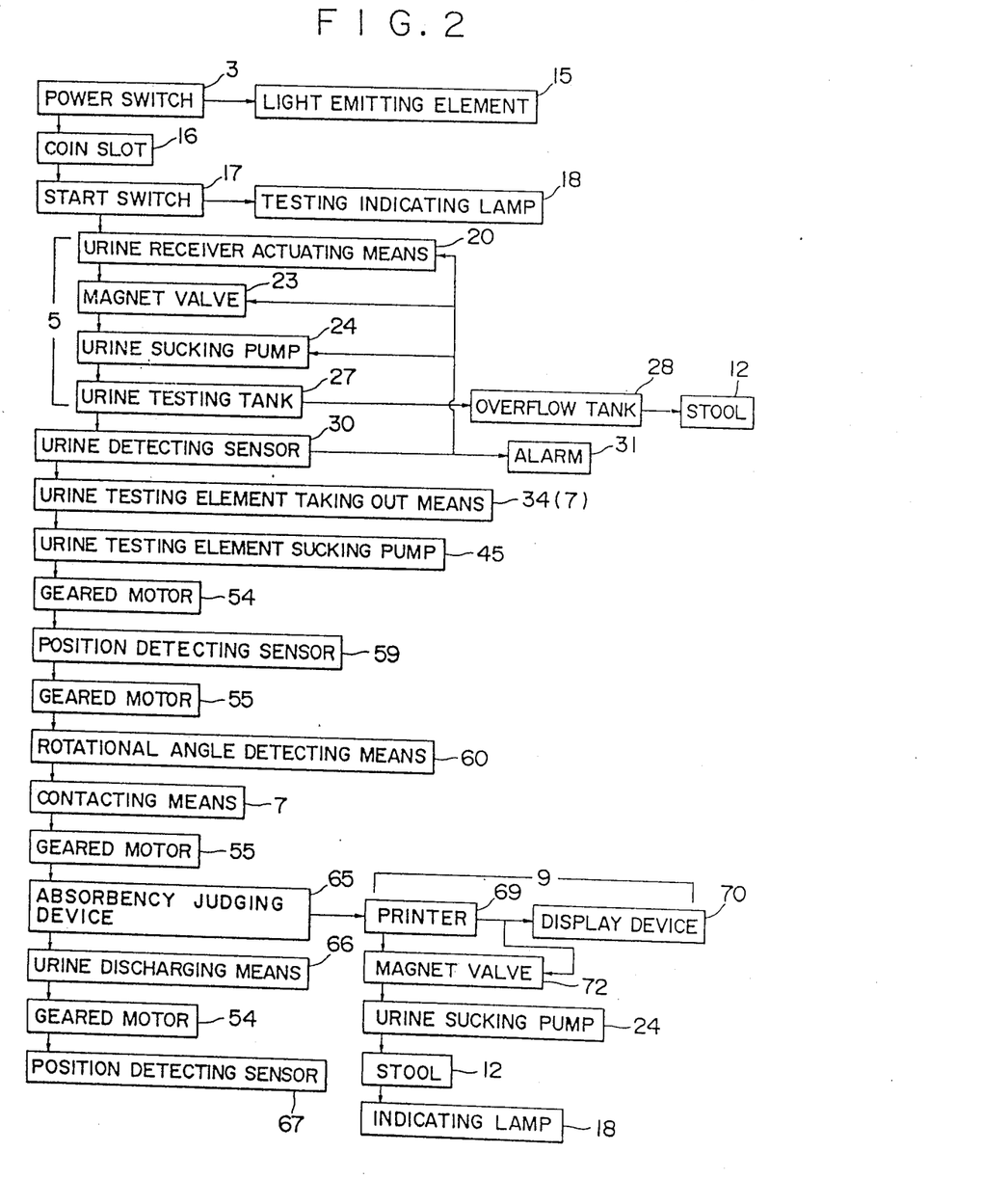
FIG. 2 is a block diagram showing more detailed construction of an automatic urinalysis system according to a first embodiment of the present invention.
Figure 3:
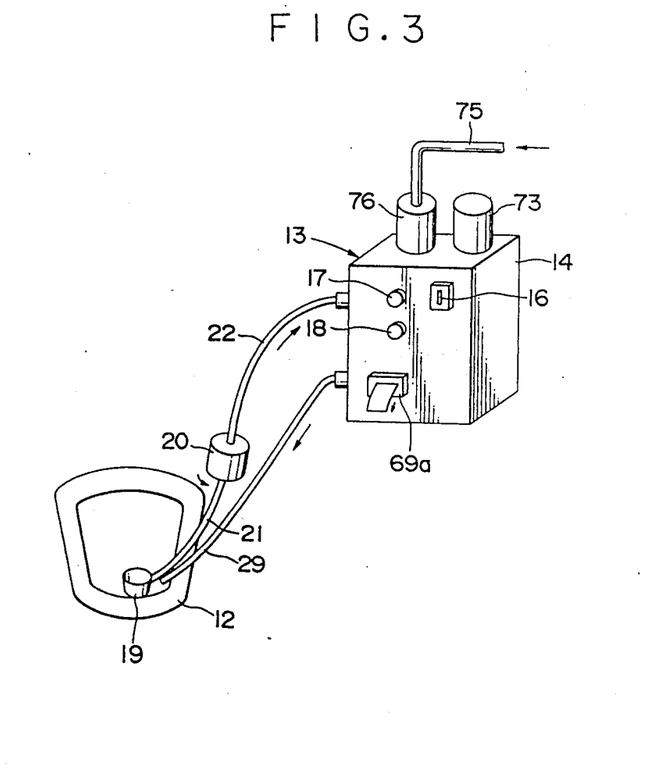
FIG. 3 is a schematic perspective view showing the automatic urinalysis system of FIG. 2 installed in connection with a stool within a toilet room.

Now, more detailed construction of the automatic urinalysis system 1 will be described in connection with a preferred embodiment of the present invention with reference to FIGS. 2 to 4.

The automatic urinalysis system 1 is installed at a stool or urinal 12 within a toilet room as such a urine excretion site 2. In particular, an automatic urinalysis system unit 13 of the system 1 is installed at a suitable location within a toilet room. The power switch 3 though not shown in FIG. 3 nor in FIG. 4 is located on a body 14 of the automatic urinalysis system unit 13 and is normally held in a closed position so as to allow use of the system 1. In order to indicate that the system 1 can be used, a light emitting element 15 shown only in FIG. 2 located on the body 14 is normally held in a lit condition. A coil slot 16 is formed in the body 14 so that use of the present system may be enabled by throwing a coin into the coin slot 16. A start switch 17 is also located on the body 14, and as the switch 17 is closed, a testing indicating lamp 18 is lit and at the same time the present system 1 starts its operation. Thus, if a subject closes the switch 17, a urine receiver actuating device 20 of the urine collecting means 5 is driven to cause a urine receiver 19 to prepare to directly receive urine excreted into the stool 12 by the subject or to receive mixture of such urine with some other liquid such as water. Here, the measuring method to be employed may be different whether the sample is urine or a mixture containing urine therein. However, it is actually preferable to collect and test urine only. But where the amount of urine for testing is too small to measure the urine, it may also be possible to measure a mixture of urine in which water is mixed at a predetermined ratio, or depending upon an item of testing, to measure a mixture of urine in which a medicine such as a medical fluid is contained. Accordingly, the sample of urine is either pure urine or a mixture (liquid) containing urine therein. However, since it is conventional to only collect pure urine, such urine sample consisting of pure urine or a mixture containing urine will be hereinafter referred to only as "urine". The urine receiver 19 is in the form a cup-shaped vessel and is supported such that it may receive urine therein only when a test of urine is to be effected during use of the toilet, that is, only when the start switch 17 is closed. Such a supporting manner may be attained by various means: for example, when a toilet 12A is not in use, a urine receiver 19A may normally be held at a position at which it cannot receive urine, for example, at a position below a seat of the stool, and only when the toilet is used and a test of urine is to be effected, the urine receiver 19A may be moved to a position at which it can receive urine. In the present embodiment, the urine receiver 19 and the actuating device 20 therefor are interconnected by a collecting pipe 21 such that, as a rotary motor built in the actuating device 20 rotates, the urine receiver 19 may be driven by the motor by way of a wire extending within the pipe 21. Thus, only when the toilet is used and a test of urine is to be effected, the urine receiver 19 is rotated or turned until its opening is directed upwardly so that it can receive urine therein. Here, the urine receiver 19 may have any form or shape only if it has an action to receive therein a required amount of urine upon collection of the urine, and for example, the urine receiver 19 may be in the form of a cup-shaped vessel having a small hole formed in a bottom wall thereof. In the case of such a vessel as just described, it need not be rotated or turned over because urine collected in the vessel will flow out via the small hole. The actuating device 20 is connected to an introducing pipe 22 which constitutes a guiding means. The introducing pipe 22 is connected to a urine sucking pump 24 via a magnet valve 23 located in the body 14. After preparation for reception of urine has been completed by operation of the actuating device 20, the magnet valve 23 is opened by a magnet valve actuating device not shown so that urine within the urine receiver 19 is sucked by the urine sucking pump 24 by way of a connecting pipe 25 and is then fed into a urine reservoir (hereinafter referred to as urine testing tank) 27 located in a testing zone within the automatic urinalysis system unit body 14 via another connecting pipe 26 connected to the pump 24. Urine which overflows the urine testing tank 27, if any, will flow into an overflow tank 28 and then be discharged into the stool 12 by way of an output pipe 29 connected to the tank 28. The urine testing tank 27 is connected to the output pipe 29 via a discharging pipe 77, a magnet valve 79 and another discharging pipe 78. Accordingly, if the magnet valve 79 is opened after completion of an intended test of urine, the urine within the urine testing tank 27 will be discharged into the stool 12 via the discharging pipe 77, magnet valve 79, discharging pipe 78 and output pipe 29.

A level sensor 30 is provided for detecting whether or not a predetermined amount of urine has been supplied into the urine testing tank 27 via the connecting pipe 26, and when the urine testing tank 27 is not filled with the predetermined amount of urine, the level sensor 30 delivers a signal to an alarm 31 so as to urge a subject to further supply urine to the urine receiver 19 using, for example, an alarming sound of a buzzer or a visual indication of a display device. Then, if urine is supplied, the urine receiver 19 is returned to its initial condition by the urine receiver actuating device 20, and then the magnet valve 23 is closed and operation of the urine sucking pump 24 is stopped. Thus, after a sufficient amount of urine has been stored into the uring testing tank 27, a urine testing element 33 is taken out from within a urine testing element containing box 32 by a urine testing element taking out means 34. While such a urine testing element may be either urine testing paper or a urine testing reagent as described hereinabove, urine testing paper is used in the present embodiment. The inside of the urine testing element containing box 32 is controlled in humidity and temperature so that it may be maintained in a predetermined dried temperature condition, and it is formed as an enclosed chamber. A number of urine testing elements 33 in the form of testing paper are accumulated in layers within the box 32 as shown in FIG. 4. Referring to FIG. 5, each of the urine testing elements 33 consists of a thin flexible rectangular substrate 35 made of a plastics material and a plurality of urine testing pieces 36 applied in a spaced relationship to the substrate 35. Preferably, the urine testing pieces 36 of the urine testing elements 33 have a sufficient thickness so that where the urine testing elements 33 are placed one on another in layers, a sufficient gap is formed between the substrates 35 of each adjacent urine testing elements 33 and between each adjacent urine testing pieces 36 to allow a taking out pin 37 to be inserted thereinto. Such taking out pins 37 are connected for actuation by the urine testing element taking out means 34. Thus, if engaging portions not shown of the taking out pins 37 are engaging with the substrate 35 of a urine testing element 33 and then the taking out pins 37 are retracted, the urine testing element 33 can be readily taken out from within the box 32. To the contrary, where the urine testing pieces 36 of the urine testing elements 33 have a relatively small thickness, a urine testing element 33 can be readily taken out from within the box 32 by pressing against the substrate 35 or the testing piece or pieces 36 of the urine testing element 33 with the taking out pins 37. The urine testing element taking out means 34 may be conveniently composed of an inexpensive plunger. A taking out pin mounting member 39 is securely mounted on an output shaft 38 of the plunger 34, and a plurality of such taking out pins 37 as described above are mounted in a suitably spaced relationship on the taking out pin mounting member 39. It is to be noted that when the plunger 34 is driven, a door of the containing box 32 is automatically opened to allow the plunger 34 to take out a urine testing element 33 outwardly of the box 32. The urine testing element 33 thus taken out from within the box 32 by the plunger 34 is then placed onto a urine testing element receiving table 40 by a suitable means. The receiving table 40 has a plurality of sucking holes 41 formed therein, and the sucking holes 41 are connected to a urine testing element sucking pump 45 via a pipe portion of a shaft 42, another pipe portion of a connecting member 43 and a connecting pipe 44. Accordingly, the urine testing element 33 placed on the receiving table 40 is attracted and secured to the receiving table 40 by vacuum caused by the sucking pump 45. A sucking magnet valve 80 is interposed between connecting pipes 44a, 44'a which are connected in series between the connecting pipe 44 and the sucking pump 45. The magnet valve 80 is opened when the urine testing element 33 is to be attracted and secured to the receiving table 40 and excessive urine contained in the urine testing element 33 is to be sucked out by the sucking pump 45. Thus, as the sucking pump 45 is rendered operative, the urine testing element 33 is attracted and secured to the receiving table 40 and excessive urine in the urine testing element 33 is sucked out into the sucking pump 45 by air which is sucked by the sucking pump 45 via the sucking holes 41, the pipe portion of the shaft 42, the pipe portion of the connecting member 43, the connecting pipe 44, 44a, the magnet valve 80 and the connecting pipe 44'a. The urine sucked into the sucking pump 45 is then discharged outwardly of the sucking pump 45, for example, into the stool 12, by a urine discharging mechanism not shown within the sucking pump 45. A discharging magnet valve 81 is interposed between connecting pipes 44b, 44'b, which are connected in series between the sucking pump 45 and the connecting pipe 44. The discharging magnet valve 81 is opened when the urine testing element 33 sticking to the receiving table 44 is to be removed after completion of an intended test of the urine testing element 33. Thus, the sucking pump 45 is now used as a discharging pump for supplying compressed air so that compressed air may be discharged from the sucking holes 41 of the receiving table 40 via the connecting pipe 44'b, the magnet valve 81, the connecting pipes 44b, 44, the pipe portion of the connecting member 43 and the pipe portion of the shaft 42 in order to remove the urine testing element 33 from the receiving table 40. A pair of bearings 46, 47 are formed on opposite sides of the connecting member 43 and are fitted on a pair of guide rails 48, 49, respectively, so that the connecting member 43 can move along the guide rails 48, 49. Secured to opposite ends of the guide rails 48, 49 are a pair of fixed plates 50, 51 to which a pair of support shafts 52, 53 which are each supported for rotation around its axis by a bearing not shown are secured, respectively. A pair of geared motors 54, 55 are secured in position by suitable means not shown, and a pulley 57 is secured to a rotary shaft 56 of the geared motor 54. A belt (or rope) 58 which may be, for example, a timing belt extends between the pulley 57 of the geared motor 54 and another pulley not shown secured to the fixed plate 51. The belt 58 is secured at a portion thereof either to the shaft 42 or to the bearing 46. A position detecting sensor 59 is located at a suitable fixed position, and the geared motor 54 is rotated until the position detecting sensor 59 detects the connecting member 43 or the bearing 46 or 47 in order to feed the urine testing element receiving table 40 to a position adjacent the position detecting sensor 59. The support shaft 53 is connected to an input shaft 61 of a rotational angle detecting potentiometer 60 and has a gear wheel 62 secured thereto. The gear wheel 62 is held in meshing engagement with another gear wheel 64 secured to a rotary shaft 63 of the geared motor 55. Thus, the geared motor 55 is rotated until the rotational angle detecting potentiometer 60 develops a predetermined rotational angle detection signal when the urine testing element receiving table 40 is turned over to a position in which it immerses the urine testing element 33 thereon in the urine within the testing tank 27. Then, the urine testing element 33 is held immersed in the urine within the testing tank 40 for about 2 or 3 seconds in order to cause the urine to sufficiently permeate into the urine testing element 33. Consequently, the urine testing element 33 is changed in color tone by a predetermined component of the urine. The receiving table 40 to which the urine testing element 33 immersed in the urine is secured is subsequently turned by an angle of 180 degrees back to its home position as shown in FIG. 4 by the geared motor 55 cooperating with the rotational angle detecting potentiometer 60. In this condition, the urine testing element 33 is measured by a urine measuring analyzer such as, for example, an absorbency judging device 65 for analysis of the urine. The structure of the absorbency judging device 65 will be hereinafter described, but here the absorption photometry will be described which is well known in the art as an automatic method of judging a developed color of a testing element such as a urine testing element 33. The absorption photometry is a method of measuring a ratio at which light of a wavelength zone peculiar to a developed color is absorbed by a testing element, and according to the absorption photometry, urine sticking to the urine testing element 33 can be measured and analyzed. A dry chemistry material such as a urine testing element or paper 33 is composed of a layer of high optical absorption and a layer of high light scattering. Accordingly, if a degree of absorption of light of a wave length corresponding to a color tone is measured, then a changed color tone density of the urine testing element 33 which change is caused by a reactive substance in the urine can be found out. The measurement of a degree of light absorption is also possible by measurement of light which is transmitted through a testing element (sample), but in the case of such a urine detecting element or paper 33 as described above, a measuring method involving light reflection is suitable between the urine detecting element 33 conventionally has a light reflective layer (the flexible rectangular substrate 35) on a rear face of the urine testing pieces 36.

Figure 6:
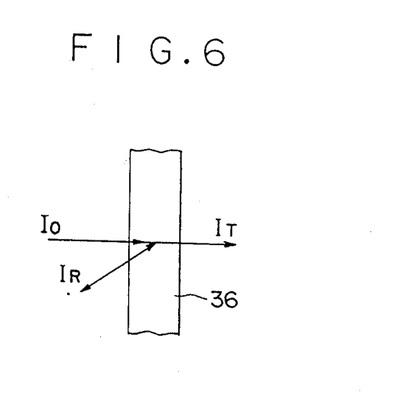
FIG. 6 is a schematic diagram illustrating a principle of measurement of a changed urine color tone density.

Now, if the amount of incident light is represented as $I_O$, the amount of reflected light as $I_R$, the amount of absorbed light as $I_A$, and the amount of transmitted light as $I_T$, then following equations stand in the optical system shown in FIG. 6:

$$I_O = I_A + I_R + I_T \tag{1}$$

$$I = \frac{I_A}{I_O} + \frac{I_R}{I_O} + \frac{I_T}{I_O} = A + R + T \tag{2}$$

where A is an absorption factor, R a reflection factor, and T a transmission factor. Since it is considered that the amount I of transmitted light is sufficiently small in a reflective optical system, the equation (1) above can be rewritten as follows:

$$I_O = I_A + I_R \tag{3}$$

Here, a (reflection) absorbency E is defined as follows:

$$E = \log \frac{I_O}{I_R} \tag{4}$$

Now, it is examined which relation stands between a density and a reflection factor of a color changing substance (the urine testing pieces 36) in a dense absorbing and scattering body having a reflective layer (the substrate 35) such as a urine testing element or paper 33 described above.

Where it can be assumed that the thickness of a scattering layer is sufficiently great and uniform, the scattering coefficient and the absorption coefficient of a scattering body at a predetermined wave length are represented as B and K, respectively. Further, if the density of scattering particles of a sample (the testing pieces 36) is represented as N, the color density of particles which have developed a color as n, the effective sectional area as S, and the scattering coefficient and the absorption coefficient of a single particle with respect to scattering light are represented as $E_K$ and $E_B$, respectively, then following expressions can be defined:

$$K = nSE_K \tag{5}$$

$$B = NSE_B \tag{6}$$

Here, if the reflection factor of the entire sample (the urine testing pieces 36) is represented as R, the equations (5) and (6) above are indicated as follows depending upon the Kubelka and Munk's law (refer to Kubelka, P. and Munk, F, Z TEC. Physik, 12593 (1981)):

$$\frac{K}{B} = \frac{(1-R)^2}{2R} = F(R) \tag{7}$$

From the expressions (5) to (7) above, $$B_n = \frac{1}{2} \left( \frac{I_O}{I_R} + \frac{I_R}{I_O} \right) - 1 \tag{8}$$

where B is a constant, and R is $I_R/I_O$.

Accordingly, if the amount $I_R$ of reflected light is measured, then the density n can be readily calculated from the equation above.

While the method of measuring a color density of a urine testing element has been described above, the expressions above are introduced under idealized conditions. Actually, using a reagent liquid having a known density, a characteristic curve (calibration curve) of the amount $I_R$ of reflected light relative to the density n can be obtained by actually measuring reflected light from a testing element 33. It is very convenient if a two-wavelength method is employed in order to compensate for muddiness of testing liquid or urine, for variations of reflected light of a wave length not selected and for other variations in measurement caused by drifts of the system. Now, the two-wavelength method will be described.

If the F(R) functions of the expression (7) above obtained from a peak wave length $\lambda_1$ of an objective substance (the testing element 33) and a reference wave length $\lambda_2$ (of the testing liquid) are represented as $F\lambda_1$, $F\lambda_2$, respectively, then $$F\lambda_1 = \beta \cdot n'\lambda_1 = \beta(n\lambda_1 + n) \tag{9-1}$$

$$F\lambda_2=\beta.n'\lambda_2=\beta(n\lambda_2+n) \quad (9\text{-}2)$$

where n is a base line density which is constant between $\lambda_1$ and $\lambda_2$, and $n\lambda_1$ and $n\lambda_2$ are densities at $\lambda_1$, $\lambda_2$, respectively and wherein $n\lambda_1 < n\lambda_2$.

From the expressions (9-1), (9-2) above, $$\Delta F=F\lambda_1-F\lambda_2=\beta(n\lambda_1-n\lambda_2) \quad (10)$$

From the expression (10) above, it can be seen that $\Delta F$ increases in proportion to a difference in density between $\lambda_1$ and $\lambda_2$. Accordingly, it can be recognized that stabilized measured values can be obtained if a calibration curve $\Delta F - n$ is produced.

It is a matter of course that the same object can be attained even if calibration curves of the difference $\Delta E$ of the absorbency E shown by the equation (4) and the density are produced depending upon actual measurement.

The absorbency judging device 65 for realizing the absorption photometry described above (the device 65 denotes the changed urine testing element color tone density measuring device and will be hereinafter referred to as changed color tone density measuring instrument) utilizes an optical system part for measuring a density of reflected light by a two-wavelength integrating sphere method. A light measuring means basically employs an integrating sphere arrangement wherein light is irradiated in a vertical direction while a light receiver is located on a side wall. The urine testing element 33 is laid horizontally on the receiving table 40 as described hereinabove, and the testing pieces 36 for 6 items are applied to the substrate (strip) 35 of the testing element 33. Light must be irradiated vertically upon the testing element 33. To this end, a light source 82 such as a tungsten filament lamp, a slit providing body 84 having a slit 83 formed therein, a lens system 86 including a set of optical lenses 85, a rotary filter disk 87, and an integrating sphere 90 having slits 88, 89 formed in upper and lower walls thereof are located from above to below in the order as listed. The inner wall of the integrating sphere 90 is formed by a layer of powder of magnesium oxide MgO or a like substance so that it may scatter and multiple reflect light. A light measuring station 91 is formed on a side wall of the integrating sphere 90. The light measuring station 91 includes a slit 92 (refer to FIG. 4) formed in a side wall portion of the integrating sphere 90 for maintaining a measuring location optimum, and an optical sensor 93 such as a CdS cell, a photodiode or a phototransistor located in an opposing relationship to the slit 92. The optical sensor 93 develops an electric signal having a magnitude corresponding to an amount of light received. A heat ray absorbing filter is located at the slit 83. Meanwhile, the rotary filter disk 87 has a plurality of optical filters (spectral filters) 94 (refer to FIG. 4) for different wave lengths located thereon. The optical filters 94 include those for wave lengths for measurement corresponding to developed colors of various kinds of testing elements 33 or of various kinds of testing pieces 36 and one for a wave length for calibration. Accordingly, with the changed color tone density measuring instrument 65 of FIG. 7, projected light 95 from the light source 82 is first adjusted to an optical axis 96 by the slit 83 and the lens system 86 and is then separated into its spectral components whereafter it is irradiated upon the testing element 33 passing through the slits 88, 89 of the integrating sphere 90. Then, reflected light 97 of the projected light 94 reflected in accordance with a developed color condition of a testing piece 36 of the testing element 33 is introduced again into the integrating sphere 90 through the slit 89. The incident light is scattered and multiple reflected by the inner wall of the integrating sphere 90 and thus comes to the optical sensor 93 via the slit 92 formed in the side wall of the integrating sphere 90. Accordingly, the changed color tone density of the testing element 33 can be measured by the optical sensor 93. It is to be noted that where a testing element 33 has a plurality of testing pieces 36 therein, there is the necessity of measuring one after another of the testing pieces 36. Accordingly, in this instance, it is necessary to move the receiving table 40, on which a testing element 33 is placed, stepwise at predetermined time intervals along the guide rails 48, 49.

Figure 4:
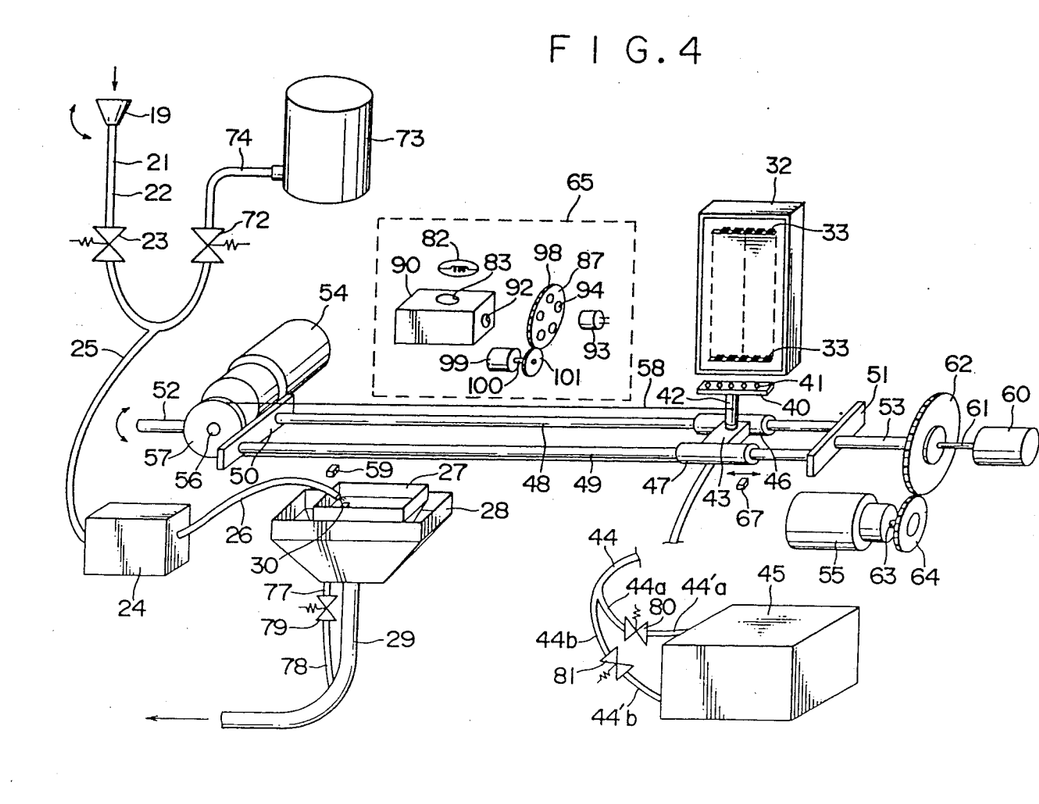
FIG. 4 is a fragmentary perspective view showing detailed construction of the automatic urinalysis system of FIG. 3.
Figure 5:
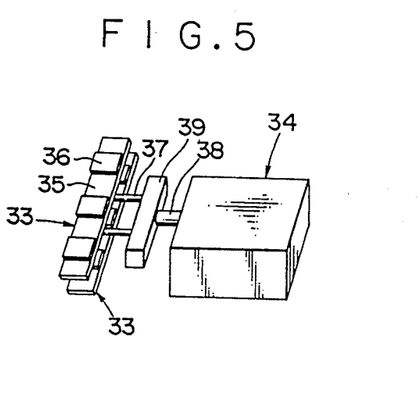
FIG. 5 is a perspective view of a urine testing element taking out means.
Figure 7:
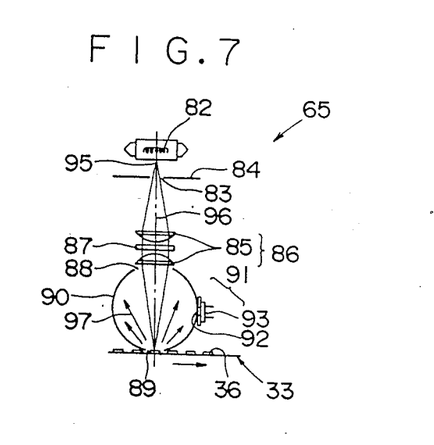
FIG. 7 is a schematic diagram illustrating an operating principle of an integrating sphere arrangement as a changed urine color tone density measuring instrument.

It is alternatively possible to use the instrument 65 as shown in FIG. 4 in place of the changed color tone density measuring instrument 65 as shown in FIG. 7. The instruments shown in FIGS. 4 and 7 have a very similar construction and are different only in location of the rotary filter disk 87. In particular, in the arrangement shown in FIG. 4, the rotary filter disk 87 is not located in the lens system 86 but is interposed between the slit 92 of the integrating sphere 90 and the optical sensor 93 as distinct from the arrangement of FIG. 7. Such location of the rotary filter disk 87 enables location in a sufficient room of means for not manually but automatically rotating the rotary disk plate 87 to enable an aimed one of the optical filters 94 to be selected at an instant.

In particular, in the changed color tone density measuring instrument 65 shown in FIG. 4, in order to automatically rotate the rotary filter disk 87, the rotary filter disk 87 has a series of gear teeth 98 formed on an outer periphery thereof and is held in meshing engagement at the gear teeth 98 thereof with a gear wheel 101 fixedly mounted on a rotary shaft 100 of a rotary motor 99. It is to be noted that the rotary motor 99 may be replaced by some other suitable means such as a rotary actuator. In order to find out a rotational angle of the rotary motor 99, a suitable means such as a rotary encoder may be employed. Further, where the rotary motor 99 is a stepping motor, the rotary filter disk 87 can be rotated by a suitable amount to select an aimed one of the optical filters 94 only by energizing the motor with a number of pulse signals corresponding to a required rotational angle. The urine testing element 33 for which measurement has been successfully completed is then taken out to a suitable location by a suitable removing means 66. In the present embodiment, the sucking pump 45 is utilized as the suitable removing means 66. In particular, after completion of the intended measurement, the sucking magnet valve 80 is closed, and then since the sucking action by the sucking pump 45 remains stopped, the discharging valve 81 is now opened and the sucking pump 45 is rendered operative to supply air so as to discharge air from the sucking holes 41 of the receiving table 40 thereby to remove the testing element 33 from the receiving table 40. The testing element 33 thus removed is then received in a storing plate not shown for storing therein testing elements 33 for which testing has been completed. Testing elements 33 stored in the storing plate can be removed from the storing plate by stopping the sucking pump 45 when the receiving table 40 is at its lower position and then by moving the receiving table 40 by means of a pin which is operated by the gravity. After then, the geared motor 54 is rotated until a position detecting sensor 67 detects the shaft 42 or the bearing 46 or 47 in order to feed the receiving table 40 back to its initial home position. After completion of the intended testing as described above, test data 68 are printed on a piece 71 of paper by a printer 69 and the printed paper is issued from an exit 69a of the printer 69. Simultaneously, measurement data 68 is indicated for a predetermined period of time on a display station 70 located on the body 14. Then, if the printed paper 71 is taken out from the printer exit 69a after completion of the indication for the predetermined period of time, then a magnet valve 72 is opened and the urine sucking pump 24 is rendered operative. Consequently, washing liquid is fed from a washing liquid tank 73 into the testing tank 27 via a connecting pipe 74, the magnet valve 72, the connecting pipe 25, the pump 24 and the connecting pipe 26. After then, the magnet valve 79 is opened to allow the washing liquid to be discharged into the stool 12 via pipes 77, 78 and 29. It is to be noted that in this instance, where a water pipe 75 is connected to the body 14 as shown in FIG. 3, the washing liquid tank 73 may be replaced by an ion-exchanger 76 for washing and sterilization interposed between the body 14 and the water pipe 76, or otherwise such as ion-exchanger 76 may be provided in addition to the washing liquid tank 73. When all the steps described above are completed, the indicating lamp 18 is extinguished. Naturally, it is a matter of course that the urine receiver 19 will accept no more urine after a required amount of urine has been collected in the course of the steps described above.

It is to be noted here that it is not essential in the present embodiment to immerse a testing element 33 into urine contained in the urine testing tank 27 as described hereinabove. In particular, it is sufficient for a urine testing element such as testing paper 33 to merely contact with urine introduced thereto. Accordingly, it may be recommendable to employ a means for dropping urine onto a urine testing element transported to a testing area.

Figure 8:
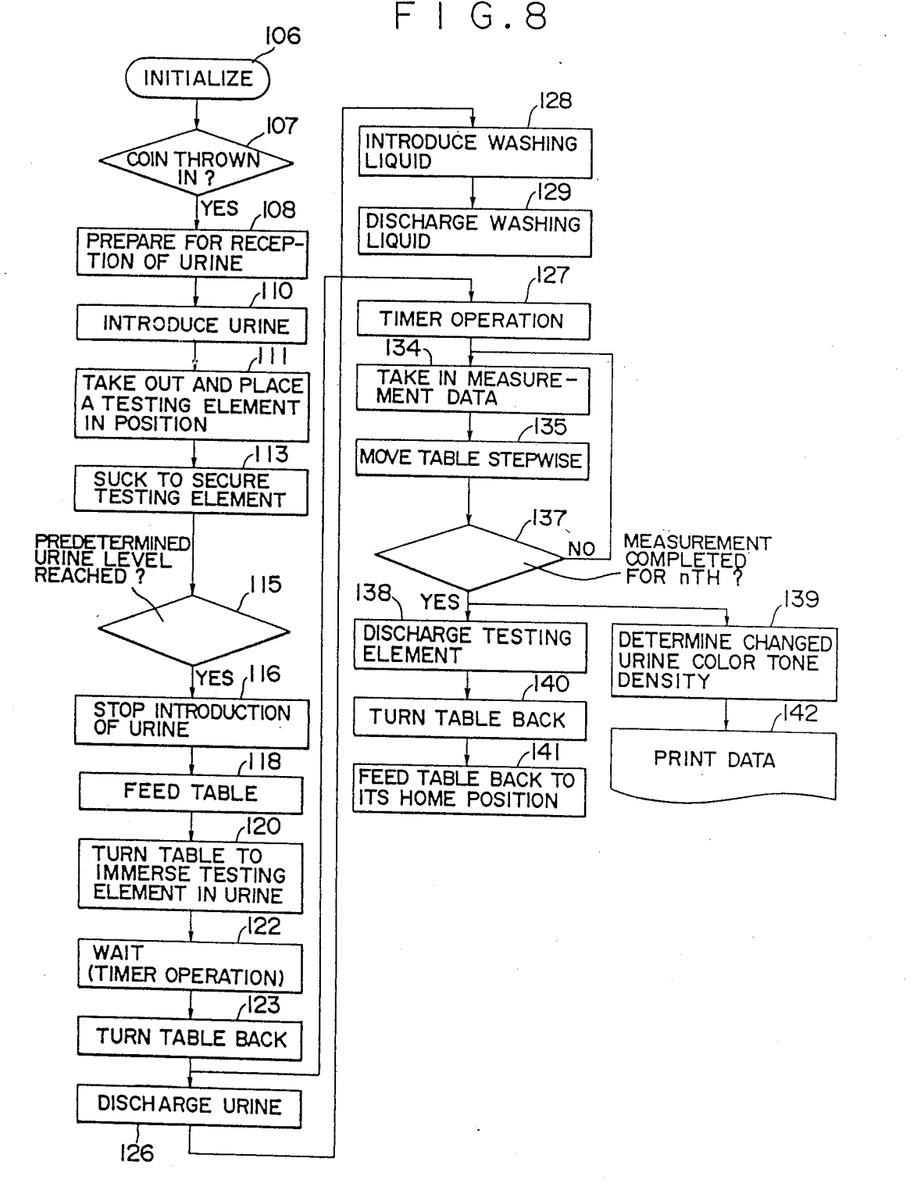
FIG. 8 is a flow chart illustrating operation of an automatic urinalysis system according to a second embodiment of the present invention.
Figure 9:
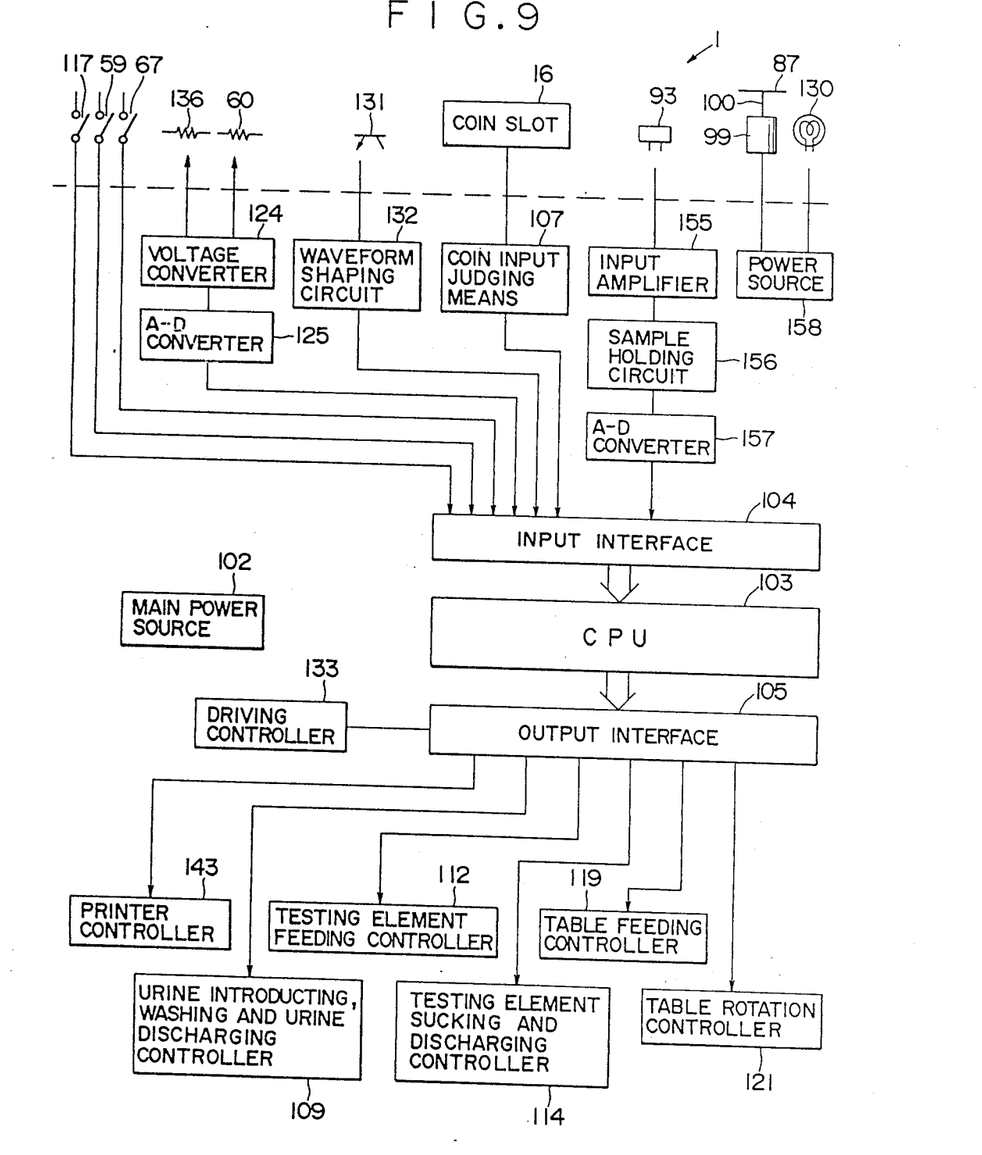
FIG. 9 is a block diagram showing the automatic urinalysis system of the second embodiment of the present invention.

Now, a second embodiment of the present invention wherein a microcomputer is employed as a controlling circuit for the system will be described with reference to a flow chart of FIG. 8 and a block diagram of FIG. 9. Since the present embodiment has a similar mechanical construction to the preceding embodiment, like parts or elements are denoted by like reference numerals to those of the preceding embodiment, and overlapping description thereof will be omitted herein.

The automatic urinalysis system 1 shown includes a main power source 102 for driving the entire system 1. The system 1 further includes a central processing unit (CPU) 103 of a microcomputer, an input interface 104, and an output interface 105. The main power source 102 is closed at a same time when a power switch 3 (refer to FIGS. 1 and 2) is closed, and upon closing of the main power source 102, a light emitting element (indicating lamp) 15 located on an automatic urinalysis system unit body 14 (refer to FIG. 3) is lit. Simultaneously, the microcomputer is rendered operative. Thus, at first, the CPU 103 initializes the input and output interfaces 104 and 105 and required portions thereof at an initializing step 106 in FIG. 8. Then, when a start switch 17 is closed, the CPU 103 advances its operation sequence to a coin input judging step 107 (FIG. 8) at which it determines from a signal received from a coin input judging means 107 (FIG. 9) via the input interface 104 whether or not a coin has been thrown into a coin slot 16. Then, in case a coin has been thrown in, the CPU 103 advances its operation sequence to a urine reception preparing step 108 at which it instructs a urine introducing, washing and urine discharging controlling means 109 to drive a urine receiver actuating device 20 to move a urine receiver 19 to a position in which urine can be introduced into the urine receiver 19. Subsequently, the CPU 103 advances its operation sequence to a urine introducing magnet valve and urine sucking pump driving step 110 at which a magnet valve 23 is opened and a urine sucking pump 24 is driven in order to feed the urine received in the urine receiver 19 into a urine testing tank 27 by way of pipes 21, 22, the magnet valve 23, another pipe 25, the pump 24 and a further pipe 26. Urine which has overflowed the urine testing tank 27, if any, is discharged into a stool 12 via an overflow tank 28 and a pipe 29. The CPU 103 then advances its operation sequence to a testing element feeding step 111 at which it delivers via the output interface 105 a signal to instruct a testing element feeding controlling circuit 112 to cause a plunger employed as a urine testing element taking out means 34 to take out a urine testing element 33 in the form of a piece of paper from within a urine testing element storage box 32 and place the thus taken out urine testing element 33 onto a urine testing element receiving table 40. After then, the CPU 103 advances its operation sequence to a testing element sucking step 113. At step 113, a urine testing element sucking and discharging controlling circuit 114 is rendered operative in response to a signal received from the CPU 103 via the output interface 105 so that a magnet valve 80 is opened and a urine testing element sucking pump 45 is driven to fixedly attract the testing element 33 to the receiving table 40 by vacuum. In this condition, at a subsequent urine level sensor judging step 115, the CPU 103 determines from a signal from a urine detecting sensor 30 whether or not the urine testing tank 27 is filled to a predetermined level in height with urine. In case the predetermined level is not reached, the CPU 103 controls, via the output interface 105, an alarm not shown to operate so as to urge a subject to excrete again. To the contrary, in case it is determined at the urine level sensor judging step 115 that the urine testing tank 27 is filled to the predetermined level with urine, the CPU 103 advances its operation sequence to a urine introducing magnet valve and urine sucking pump stopping step 116 at which the magnet valve 23 is closed and the urine sucking pump 24 is stopped. It is to be noted that in case the CPU 103 detects from a signal from a testing element presence detecting switch 117 that there remains no testing element 33 in the box 32 when a testing element 33 is to be taken out from within the box 32 by the plunger 34 at the testing element feeding step 111, the CPU 103 controls the urine introducing, washing and urine discharging controlling means 109 to operate to automatically set extra testing elements in position into the box 32. When there is no extra testing element, the alarm operates to give a warning of it. After such stopping of the magnet valve 23 and the urine sucking pump 24, the CPU 103 advances its operation sequence to a testing element receiving table feeding step 118. At the step 118, the CPU 103 instructs a testing element receiving table feeding controlling circuit 119 to control a geared motor 54 to rotate until the receiving table 40 is fed to a position adjacent a position detecting sensor 59. After then, the CPU 103 advances its operation sequence to a urine immersing step 120 at which a receiving table rotation controlling circuit 121 is instructed to control another geared motor 55 to turn the receiving table 40 by an angle of 180 degrees to a position in which the testing element 33 fixed to the receiving table 40 is immersed in the urine contained in the testing tank 27.

Subsequently, the CPU 103 advances its operation sequence to a timer operating step 122 at which it waits, using an internal timer thereof, for a suitable period of time, for example, for three minutes, in order to keep the condition in which the testing element 33 is immersed in the urine contained in the testing tank 27. After lapse of the time, the CPU 103 instructs, at a receiving table returning step 123, the controlling circuit 121 to control the geared motor 55 to rotate now in the opposite direction in order to return the receiving table 40 to its initial home position. It is to be noted that by what amount and in which direction the geared motor 55 must rotate in order to rotate the receiving table 40 depends upon a signal from a rotational angle detecting potentiometer 60. A rotational angle signal from the potentiometer 60 is converted into a suitable analog signal by a voltage converting circuit 124 and further into a digital signal by an analog to digital converter 125. The digital signal is thus fed back to the controlling circuit 121 via the input interface 104, CPU 103 and output interface 105. Since the testing element 33 immersed in urine is changed in color tone and density by a component of the urine, the changed urine color tone density can be measured in succeeding steps. Thus, the CPU 103 advances its operation sequence either to a urine discharging magnet valve driving step 126 or to a measuring timer operating step 127. The urine discharging magnet valve driving step 126 will be described first. In particular, after starting of the returning movement of the receiving table 40 at the receiving table returning step 123, the CPU 103 instructs the controlling circuit 109 to control a magnet valve 79 to operate so as to allow the urine within the testing tank 27 to be discharged into the stool 12 via a pipe 77, the magnet valve 79 and pipes 78 and 29. After then, the CPU 103 advances its operation sequence to a washing liquid introducing step 128 at which a magnet valve 72 is opened by the controlling circuit 109 and the urine sucking pump 24 is driven for about 5 seconds so that washing liquid within a washing liquid tank 73 may be introduced by a predetermined amount into the testing tank 27 via a pipe 74, the magnet valve 72, the pipe 25, pump 24 and pipe 26. After then, the CPU 103 advances its operation sequence to a washing liquid discharging step 129 at which the magnet valve 79 is driven for about 5 seconds by the controlling circuit 109 so that the washing liquid within the testing tank 27 may be discharged into the stool 12 via the pipe 77, magnet valve 79 and pipes 78, 29. After completion of the returning movement of the receiving table 40 at the receiving table returning step 123, a changed urine color tone density measuring instrument 65 is rendered operative to test and measure the testing element 33. After then, the CPU 103 advances its operation sequence to the measuring timer operating step 127 at which such measurement as described above is carried out for about 20 seconds. While it is already described hereinabove that in this instance a required one of optical filters 94 of a rotary filter disk 87 of the measuring instrument 65 must be selected, it is necessary in this instance to find a rotational angle of the rotary filter disk 87. To this end, the rotary filter disk 87 has a series of slits formed along an outer periphery thereof, and a light source 130 such as a light emitting diode and an optical filter position sensor 131 such as a phototransistor or a photodiode are located in an opposing relationship via such a slit of the rotary filter disk 87. A photo-interrupter may conveniently be used for such optical means. A power source 158 such as a battery is connected to supply power to the light source 130. Thus, a signal from the filter position sensor 131 is shaped in wave form by a waveform shaping circuit 132 and transmitted to a driving controlling circuit 133 via the input interface 104, CPU 103 and output interface 105. Consequently, a motor 99 is controlled to rotate by a selected angular distance to bring a selected one of the optical filters 94 to a predetermined position for measurement, thereby allowing measurement of various objects. Measurement data is developed from an optical sensor 93 of the measuring instrument 65 and transmitted to the input interface 104 via an input amplifier 155, a sample holding circuit 156 and an analog to digital converter 157. Thus, the CPU 103 reads, at a measurement data reading step 134, a signal from the analog to digital converter 157 via the input interface 104. After completion of the testing of a single testing piece 36 of the testing element 33 with the optical filters 94, the CPU 103 subsequently advances its operation sequence to a receiving table stepwise feeding step 135 at which the controlling circuit 112 controls the geared motor 54 to rotate until a predetermined signal is produced from a feeding amount detecting potentiometer 136 within the geared motor 54 in order to feed the receiving table 40 to a position at which a subsequent next testing piece 36 can be measured. Such a sequence of operations as described above will be repeated until after completion of testing of all of the testing pieces 36 of the testing element 33 with the optical filters 94. After completion of the stepwise feeding step 135, the CPU 103 advances its operation sequence to a measurement completion judging step 137. In particular, at the judging step 137, it is judged whether or not, where the testing element 33 has up to n testing pieces 36, n times of measurement have been completed, and in case such n times of measurement have not yet been completed, the CPU 103 returns its operation sequence to the measurement data reading step 134. After completion of the n times of measurement, the CPU 103 advances its operation sequence to a testing element discharging step 138 and then to a changed urine color tone density judging step 139. At first at the testing element discharging step 138, the controlling circuit 121 controls the geared motor 55 to rotate a predetermined amount in accordance with a signal from the potentiometer 60. A receiving plate not shown is provided at this position. Since in this condition the magnet valve 80 is in its closed position under the control of the controlling circuit 109, the sucking action of the testing element 33 to the receiving table 40 by the pump 45 is at rest. Thus, under the control of the controlling circuit 109, a magnet valve 81 is opened and the pump 45 is rendered operative so that air is now discharged from sucking holes 41 via a pipe 44'b, the magnet valve 81, another pipe 44b and so on. Consequently, the testing element 33 on the receiving table 40 is removed from the receiving table 40 and received into the receiving plate not shown. After then, the CPU 103 advances its operation sequence to a receiving table returning step 140. At the returning step 140, the controlling circuit 121 operates in response to a signal from the potentiometer 60 to control so as to turn the receiving table 40 to its original upright position. Subsequently, the CPU 103 advances its operation sequence to a receiving table home position returning step 141 at which the geared motor 54 rotates under the control of the controlling circuit 121 until a position detecting sensor 67 detects a predetermined portion of an element which moves together with the receiving table 40. As a result, the receiving table 40 is returned to its initial home position. Now, advancement from the measurement completion judging step 137 to the changed urine color tone density judging step 139 will be described. At the density judging step 139, the CPU 103 corrects data signals received from the various testing pieces 136 of the testing element 33 via the input interface 104 and outputs the thus corrected data signals to a printer controlling circuit 143 via the output interface 105. Then, the CPU 103 advances its operation sequence to a printing step 142 at which the printer controlling circuit 143 controls a printer 69 not shown to print the received measurement test data onto a print medium or paper 71 and then send out the print paper 71 from a printer exit 69a.

With such a sequence of operations as described above, the automatic urinalysis system of the present embodiment can automatically test and measure urine.

As apparent from the foregoing description, where an automatic urinalysis system according to the present invention is installed at a urine excretion site such as a toilet of a hotel, a department store, a firm or a house of a subject itself, urine can be tested and analyzed at any time or frequently by any individual without the help of a doctor or a nurse and without soiling a hand of the subject. Thus, health care can be managed depending upon analyzed information of urine provided by the automatic urinalysis system.

Having now fully described the invention, it will be apparent to one of ordinary skill in the art that may changes and modifications can be made thereto without departing from the spirit and scope of the invention as set forth herein.

What is claimed is:

1. An automatic urinalysis system for use at an excretion site by a subject who desires to have their urine analyzed, comprising:
a sample collecting means for collecting a sample of urine directly from the subject during urination at an excretion site at which said automatic urinalysis system is installed and for taking the collected urine sample into said automatic urinalysis system;
a guiding means for receiving the urine sample directly from said sample collecting means and for introducing the urine sample into a testing area within a body of said automatic urinalysis system;
a urine testing element located within said body;
a contacting means for automatically contacting said urine testing element with the urine sample in the testing area;
a urine testing element measuring means for automatically measuring at least one parameter of said urine testing element contacted with the urine sample by said contacting means;
a display means for displaying test data from said urine testing element measuring means; and
a discharging means for discharging the urine sample to a discharge location after the urine sample has been contacted by said urine testing element;
said sample collecting means being provided within a urinal.

2. An automatic urinalysis system as claimed in claim 1, wherein said sample collecting means comprises a cup-shaped urine receiving vessel having an opening and which is arranged for movement between operative and inoperative conditions such that when said vessel is in said inoperative condition, said opening thereof is directed downwardly and said vessel is turned to a position in which said opening thereof is directed upwardly in said operation condition.

3. An automatic urinalysis system as claimed in claim 2, wherein said urine receiving vessel is connected to be driven by a rotary motor.

4. An automatic urinalysis system as claimed in claim 3, wherein said urine receiving vessel is driven by way of a wire connected to said motor.

5. An automatic urinalysis system as claimed in claim 4, wherein said wire is located in a duct including a pipe for sucking a sample of urine to the testing area therethrough.

6. An automatic urinalysis system as claims in claim 1, wherein a plurality of such urine testing elements are located within said body of said automatic urinalysis system, and said contacting means includes means for taking out said urine testing element one by one from within said body.

7. An automatic urinalysis system as claimed in claim 6, wherein said means for taking out said urine testing elements includes a plunger.

8. An automatic urinalysis system as claimed in claim 6, wherein said urine testing elements are located in a urine testing element containing box within said body.

9. An automatic urinalysis system as claimed in claim 8, wherein said urine testing element containing box is controlled in temperature and humidity.

10. An automatic urinalysis system as claimed in claim 1, wherein said contacting means includes a urine reservoir located in the testing area, and means for feeding said urine testing element to immerse the same into the urine sample in said urine reservoir.

11. An automatic urinalysis system as claimed in claim 10, further comprising means for washing or sterilizing said urine reservoir.

12. An automatic urinalysis system as claimed in claim 1, wherein said contacting means includes means for dropping the urine sample to said urine testing element fed to the testing area.

13. An automatic urinalysis system as claimed in claim 12, wherein said urine testing element measuring means includes an absorption photometer for measuring a changed color tone density of said urine testing element.

14. An automatic urinalysis system as claimed in claim 1, wherein said urine testing element is changed in color by a component of the urine sample as said urine testing element is contacted by the urine sample.

15. An automatic urinalysis system as claimed in claim 14, wherein said urine testing element is urine testing paper.

16. An automatic urinalysis system as claimed in claim 15, wherein a plurality of such urine testing elements are located one on another within a urine testing element containing box within said body of said automatic urinalysis system.

17. An automatic urinalysis system as claimed in claim 1, wherein said contacting means includes a feeding means for feeding said urine testing element to the testing area, said feeding means including a movable urine testing element receiving table and means for attracting and holding said urine testing element to said urine testing element receiving table.

18. An automatic urinalysis system as claimed in claim 17, wherein said means for attracting and holding includes a mechanism for discharging urine or a mixture containing urine which sticks to said urine testing element receiving table outwardly of said means for attracting and holding.

19. An automatic urinalysis system as claimed in claim 17, wherein said means for attracting and holding said urine testing element to said urine testing element receiving table includes a tube extending between said urine testing element receiving table and said means for attracting and holding said urine testing element.

20. An automatic urinalysis system as claimed in claim 19, wherein said tube has a valve interposed therein for allowing compressed air to be supplied therethrough in order to remove said urine testing element after a test has been completed using said urine testing element in addition to a valve which is used when said urine testing element is to be attracted and held to said urine testing element receiving table by said means for attracting and holding.

21. An automatic urinalysis system as claimed in claim 20, wherein each of said valves is a magnet valve.

* * * * *